United States Patent [19]

Cazares

[11] Patent Number: 4,842,696
[45] Date of Patent: Jun. 27, 1989

[54] PURIFICATION OF PENTACHLORONITROBENZENE BY DISTILLATION

[75] Inventor: Arturo S. Cazares, Norte, Mexico

[73] Assignee: Quimica Organica De Mexico, S.A. De C.Y.

[21] Appl. No.: 105,677

[22] Filed: Oct. 8, 1987

[51] Int. Cl.[4] .......................... B01D 3/34; C07C 79/10
[52] U.S. Cl. ........................................ 203/49; 203/91; 203/DIG. 2; 203/DIG. 11; 568/938
[58] Field of Search ............... 203/91, 49, 39, 99, 203/DIG. 2, DIG. 11; 568/938; 202/153, 176, 177

[56] References Cited

U.S. PATENT DOCUMENTS

| | | | |
|---|---|---|---|
| 2,795,621 | 6/1957 | Bloom | 568/938 |
| 3,144,476 | 8/1964 | Ten Haken | 568/938 |
| 3,549,504 | 12/1970 | Adica et al. | 203/49 |
| 4,026,955 | 5/1977 | Breaux et al. | 568/938 |
| 4,064,147 | 12/1977 | Thelen et al. | 568/938 |
| 4,090,922 | 5/1978 | Bauer et al. | 203/49 |
| 4,147,732 | 4/1979 | Mendiratta | 568/938 |
| 4,289,589 | 9/1981 | Koehler et al. | 203/49 |

FOREIGN PATENT DOCUMENTS

78/95926   8/1978   Japan ..................................... 568/938

Primary Examiner—Wilbur Bascomb

[57] ABSTRACT

Pentachloronitrobenzene (PCNB) which initially contains in excess of 0.5% hexachlorobenzene (HCB) is purified by distilling the impure PCNB at a temperature between 100°–250° C. and a pressure below or at atmospheric pressure to obtain a PCNB product having a HCB content lower than 0.5%, and preferably lower than 0.1%.

18 Claims, 3 Drawing Sheets

PILOT PLANT EQUIPMENT FOR THE PCNB PURIFICATION

PILOT PLANT EQUIPMENT FOR THE PCNB PURIFICATION

PURIFICATION OF PENTACHLORONITROBENZENE BY DISTILLATION

BACKGROUND OF THE INVENTION

1. Field of the Invention

The present invention relates to a process for purifying pentachloronitrobenzene (sometimes referred to hereinafter as PCNB), by a distillation process which reduces the hexachlorobenzene (sometimes referred to hereinafter as HCB) content of the PCNB starting material to a concentration below 0.5%, and preferably to a concentration below the 0.1%. The present process also reduces the content of tetrachloronitrobenzenes (sometimes referred to hereinafter as TCNBs) and any lower chloronitrobenzenes that may have been present in the PCNB starting material to traces, thereby forming an essentially pure PCNB product.

2. Description of the Prior Art

Pentachloronitrobenzene is a commercially important fungicide for application to soil and seeds for controlling various plant diseases, specifically those caused by botrytis, fusarium, rhizoctonia and anthracnase.

Two industrial processes exist for the manufacture of PCNB. The first process, and by far the most important, involves the chlorination of nitrobenzene in chlorosulphonic acid using iodine as a catalyst. This process is described, for example, by Thurston in the "Fiat Formal Report No. 949." Lojewski, in the U.S. Pat. No. 3,026,358, disclosed a variation of this process, wherein chloronitrobenzene is used as the starting material in an attempt to reduce the final HCB content. The second commercial process for the production of PCNB is the nitration of pentachlorobenzene with nitric acid in sulfuric acid. This process is described by Breaux in U.S. Pat. No. 4,026,955, and by others, for example, U.S. Pat. Nos. 4,057,590; 4,138,438; and 4,147,732. The PCNB obtained with these prior art commercial processes, as described above, contains HCB in concentrations above 0.5%, by weight even with mild reaction conditions that severely affect productivity.

It has been demonstrated that HCB is an animal carcinogen. Consequently, the Office of Pesticides and Toxic Substances of the Environmental Protection Agency has set a deadline of Apr. 28, 1988 to industry manufacturers to implement new technologies to reduce the HCB level in PCNB to 0.1% by weight or less.

Recently, several processes for manufacturing PCNB having a reduced HCB content have been patented. Included among these processes are the conversion of HCB back to PCNB using pentachlorothiophenol (U.S. Pat. Nos. 4,454,362 and 4,461,918) and using pentachlorobenzonitrile (U.S. Pat. No. 3,984,487). While these processes do represent significant advances in producing relatively pure PCNB, they have the disadvantage of using HCB as a starting material, thereby requiring two additional steps. To date, a commercially acceptable process capable of successfully separating HCB from PCNB has not been described.

SUMMARY OF THE INVENTION

It is an object of this invention to provide a high purity PCNB from the relatively impure PCNB already obtained by conventional processes.

It is another object of this invention to provide a process which, by means of readily available distillation apparatus can provide a PCNB product having a concentration of HCB of less than 0.5% by weight and preferably less than 0.1% by weight.

Still another object of this invention is to purify PCNB having an undesirably high concentration of tetrachloronitrobenzene and/or lower chloronitrobenzes by means of distillation.

In accordance with one aspect of the invention, an essentially pure PCNB having a concentration of HCB of less than 0.5% by weight, and preferably less than 0.1% by weight, is prepared by distilling commercial or technical grade of PCNB at a temperature of about 100°–300° C., preferably from about 150° to about 300° C., and most preferably from about 150° to about 250° C., and at a pressure of up to about 1 atmosphere. The distillation produces an overhead having a higher HCB concentration then the starting PCNB and a relative pure PCNB residue.

BRIEF DESCRIPTION OF THE DRAWING

The novel features which are characteristic of the present invention are set forth with particularity in the appendant claims. However the various objects and features of the invention will be understood more clearly and fully from the following description of the invention, taken in conjunction with the drawings, in which;

DESCRIPTION OF THE INVENTION

Figure 1:
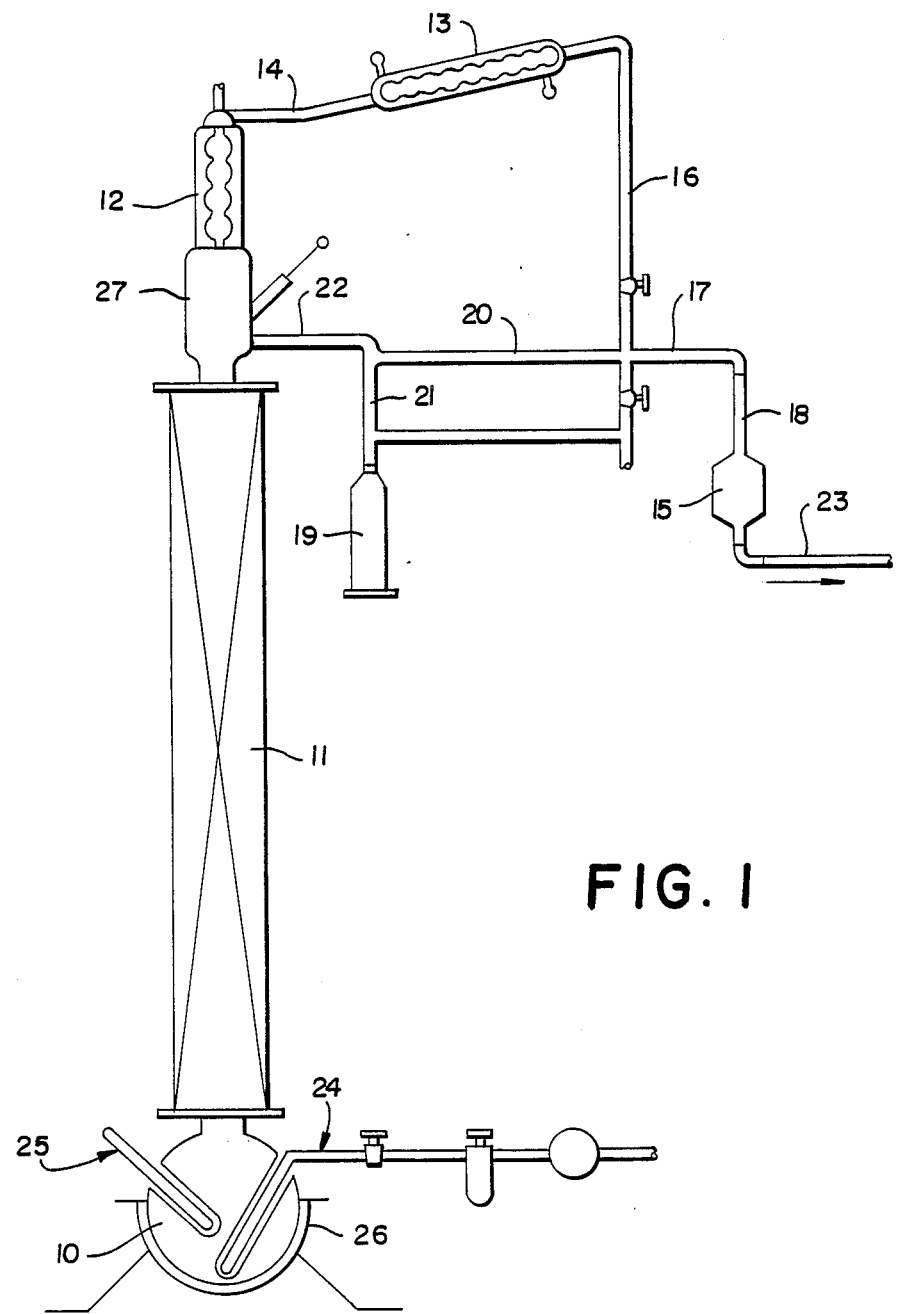
FIG. 1 is an elevational view of a pilot plant apparatus for purifying PCNB in accordance with the present invention.
Figure 2:
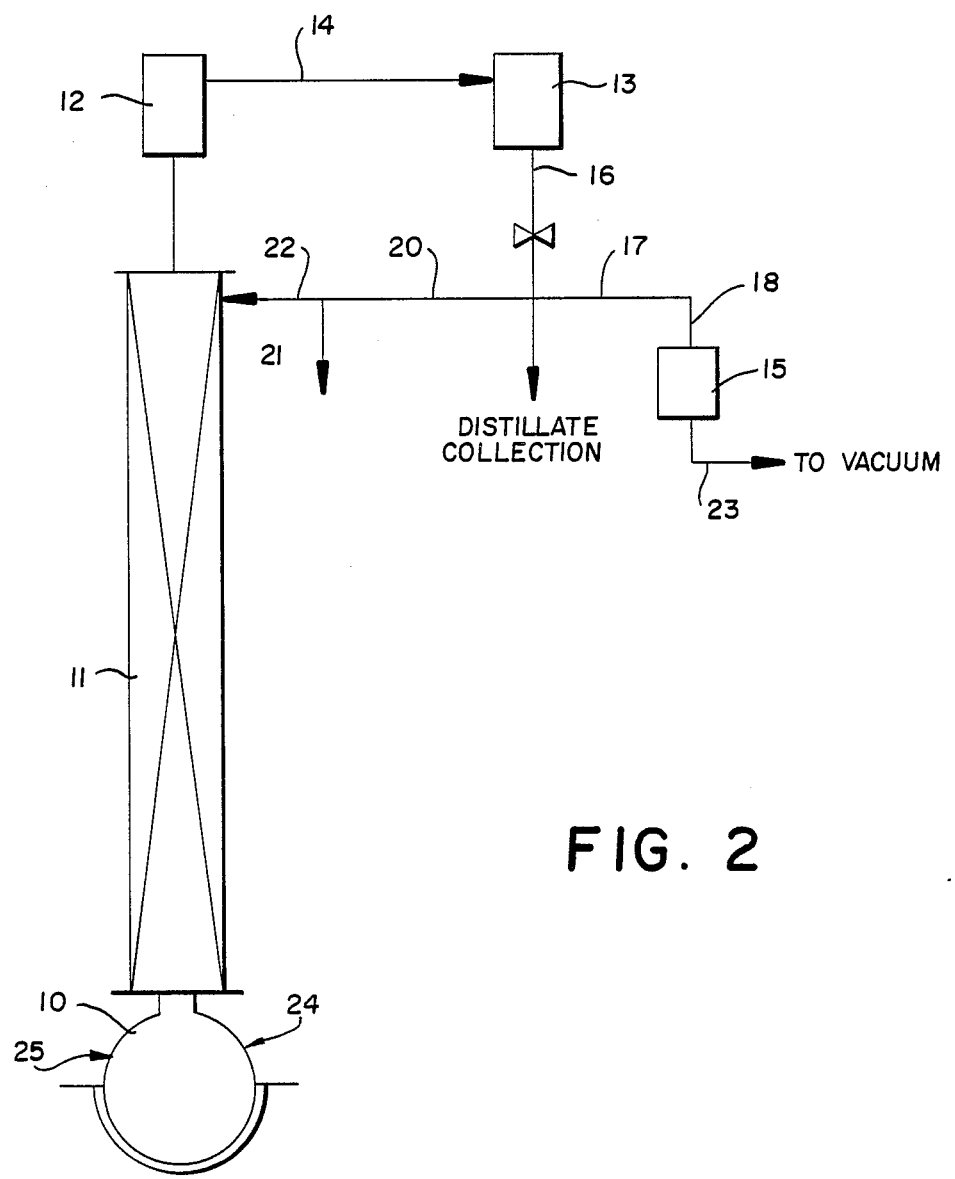
FIG. 2 is a schematic elevational view, with portions removed for the sake of simplicity of the apparatus shown in FIG. 1.

Referring to the drawings, and more particularly to FIGS. 1 and 2, there is shown a distillation apparatus for purifying a commercial or technical grade of PCNB having a high HCB content (greater than 0.5% by weight). Such commercial PCNB may also contain one or more TCNBs and various lower chloronitrobenzenes, such as trichloronitrobenzene, dichloronitrobenzene, etc.

Among possible starting materials are PCNBs prepared commercially by halogenating either nitrobenzene, or mono, di, tri, or tetrachloronitrobenzene or mixtures thereof. Other suitable PCNB starting materials may be prepared by first halogenating benzene, or mono, di, tri, or tetrachlorobenzene or mixtures thereof, followed by nitrating the resulting pentachlorobenzene. Still other usable PCNB starting materials comprise any mixture of PCNB, HCB, TCNBs, and lower chloronitrobenzenes obtained when a PCNB-forming reaction is interrupted at any stage of a PCNB-forming process.

The commercial, impure PCNB starting material is placed into a distillation vessel or flask 10 which is connected to the bottom of a distillation column 11. The column 11, which in preferred aspects of this invention is packed, for example, with conventional ceramic or stainless steel packing material, is connected to one or more condensers. In one preferred embodiment, the column 11 is connected to a vertical condenser 12 which, in turn, is connected to a horizontal condenser 13 through line 14. The horizontal condener 13 is connected to a knock out drum 15 through lines 16, 17 and 18 and to a distillate collector vessel 19 through lines 16, 20 and 21. Lines 16, 20 and 22 provide conduit means for returning refluxed overhead to the column 11. The knock out drum 15 is also connected to a vacuum source (not shown) through line 23 such that the vacuum source is in fluid communication with the distillation column 11 and the flask 10 via lines 8, 17, 20 and 22. This enables the entire system to be kept at a pressure at or below atmospheric pressure during the purification process.

The PCNB starting material is introduced with the flask 10 through line 24 and is suitable heated, for example, by means of a steam jacketed or electrically heated flask support 26. The PCNB is heated to a temperature above about 100° C. and generally above the melting point of PCNB (145° C.–300° C.). Preferably the PCNB is heated between about 150° to about 300° C., and most preferably between about 150° C. and about 250° C. to allow the PCNB to evaporate. In one aspect of the invention, this melting and evaporation step may be aided by bubbling an inert gas, such as nitrogen, through the PCNB in the flask 10, for example, by means of line 25. The distillation column 11 and all lines should be preheated to avoid condensation.

After an initial condensate is collected in vessel 19, the reflux ratio is adjusted to between about 1:1 to about 150:1, and preferably between about 80:1 to about 120:1, to assure the desired separation of HCB from the PCNB starting material.

The distillation is then continued at a rate of, for example, 1–100 ml/hr, and usually between about 5 and 20 ml/hr. Samples of the condensed distillate and the residue in the flask 10 are analyzed periodically, for example, by gas chromatography until the HCB content in the residue is below about 0.5% by weight, and preferably below 0.1% by weight. Such analyses indicate that approximately 5–70% of the PCNB starting material generally must be distilled, depending on the initial PCNB compositions to achieve a residue having a HCB content of less than about 0.1% by weight.

Figure 3:
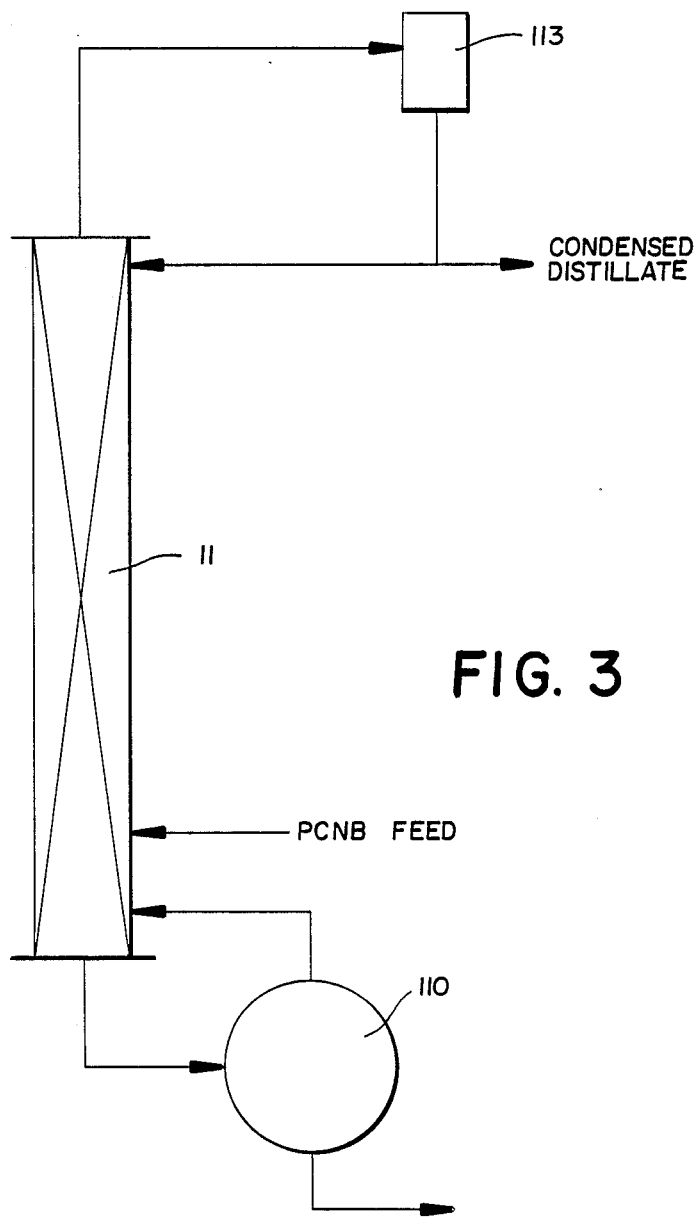
FIG. 3 is a schematic elevational view of an apparatus for the purifying PCNB on a continuous basis.

In an alternative embodiment, as illustrated schematically in FIG. 3, the present purification of PCNB may be accomplished on a continuous basis, for example, by continuously introducing inpure PCNB into the distillation column 111, while simultaneously withdrawing condensed distillate from condenser 113 and purified PCNB from reboiler 110.

The relative ease of the separation of the HCB from the PCNB starting material was unexpected since there is only a small difference in boiling points between PCNB and HCB at atmospheric pressure. The PCNB obtained as the residue in the flask 10, in all cases, analyzed for a HCB content of less than 0.5% by weight, and in most cases lower than 0.1% by weight. In some instances no HCB was detected by the known chromatographic analyses.

The invention is further illustrated, but not limited to, the following examples.

EXAMPLES 1–9

Impure PCNB was purified in the pilot plant apparatus illustrated in FIG. 1. The apparatus consisted of an adiabatic glass distillation column 11, a pyrex glass reboiler 10, pyrex glass vertical and horizontal condensers 12 and 13, respectively, and a pyrex glass distillate receptor bottle 19. The distillation column 11 was made of Podbelniak type ACE glass and had the following characteristics:

Height (cm): 210
Internal Diameter (cm): 5.1
Packing height (cm): 230
Packing type: Helipak 3008
Packing size (cm): 0.244×0.445×0.445
Packing size (in): 0.092×0.175×0.175
Packing density (kg/lt): 1.134

The packing material was stainless steel 316. This packing shows a low pressure drop and high efficiency and according to the manufacturer specifications, the number of theoretical stages for this column with the packing height above indicated is between about 60 and about 100.

The reboiler 10 was a 6 liter pyrex glass flask provided with a thermal well, a heating mantle and means for sampling the residue during the operation of the column.

The dome 27 of the column 11 was made also of pyrex glass and was provided with a thermal well and means for connecting the dome to the vertical condenser 12. The apparatus included a knock out drum 15, a vacuum source and several valves to allow the desired reflux ratio and system operating pressure.

In order to avoid product solidification, all condenser lines, and all sampling and vacuum lines were equipped with flexible electric heating tapes.

The apparatus was preheated to a temperature on the order of 200°–220° C. and the reboiler pressure was adjusted to the desired level. Technical grade (impure) PCNB was added to the reboiler which was heated to 190°–270° C. as noted in Table 1. The distillation was run at the reflux ratio noted in Table 1. For runs using total reflux, the reflux ratio was adjusted to 1:1 when samples were taken. The runs were continued until the noted amounts of distillate and residues were recovered and analyzed. The compositions of the impure PCNB, the composition of the distillate, the composition of the purified PCNB residue, the amounts of distillate and residue recovered and the operating conditions are set forth in Table 1.

It should be understood that the above examples in no way limit the scope of this invention and are intended merely as illustrations of the manner in which the present invention may be practiced. It should be obvious to one skilled in the art that the present invention is in no way limited to the removal of HCBs from PCNB by a batch procedure and that the method of the present invention contemplates numerous modifications within the spirit and scope of this invention.

TABLE 1

| EXAMPLE | OPERATING PRESSURE mm hg | CONDITIONS TEMPERATURE °C. BOTTOM | DOME | REFLUX RATIO | FEED AMT. g. | LOT:* | DISTILLATE AMT. g. | COMPOSITION TCNB | HCB | PCNB | AMT. g. | RESIDUE COMPOSITION PCNB | UN-IDENTIFIED |
|---|---|---|---|---|---|---|---|---|---|---|---|---|---|
| 1 | 50 | 218–222 | 200–214 | total | 3000 | A | 906 | 12.06 | 2.67 | 85.27 | 1919 | 99.48 | 0.52 |
| 2 | 50 | 218–222 | 208–214 | total | 3000 | B | 587 | 10.62 | 1.61 | 87.77 | 2123 | 99.56 | 0.44 |

TABLE 1-continued

| | | | | | | | | | | | | | |
|---|---|---|---|---|---|---|---|---|---|---|---|---|---|
| 3 | 40 | 214–270 | 192–208 | 90/1 | 3000 | A | 260 | 42.33 | 6.82 | 50.85 | 2544 | 99.59 | 0.41 |
| 4 | 10 | 192–210 | 175–180 | 90/1 | 3000 | B | 171 | 23.51 | 4.29 | 72.20 | 2669 | 99.64 | 0.36 |
| 5 | 10 | 190–195 | 170–185 | 120/1 | 3000 | B | 295 | 18.07 | 2.99 | 78.94 | 2564 | 99.75 | 0.25 |
| 6 | 10 | 195–200 | 160–180 | 90/1 | 3000 | C | 277 | 25.25 | 9.84 | 64.91 | 2391 | 99.7 | 0.30 |
| 7 | 10 | 195–205 | 175–190 | 90/1 | 5000 | A | 1161 | 16.47 | 3.62 | 79.91 | 3487 | 99.58 | 0.42 |
| 8 | 10 | 188–198 | 165–180 | 90/1 | 1883 | D | 1011 | 48.72 | 5.63 | 45.65 | 784 | 99.27 | 0.73 |
| 9 | 10 | 208–212 | 165–190 | 90/1 | 7011 | E | 500 | 31.34 | 8.83 | 59.83 | 6511 | 100 | — |

*Five lots (A–E) of impure PCNB were purified. The composition of each lot is set forth below:

Composition (% by weight)

| LOT | TCNB | HCB | PCNB |
|---|---|---|---|
| A | 4.37 | 0.75 | 94.80 |
| B | 2.18 | 0.46 | 97.36 |
| C | 3.36 | 1.36 | 95.11 |
| D | 26.41 | 4.67 | 68.92 |
| E | 2.83 | 0.81 | 96.36 |

What is claimed is:

1. A process for purifying impure pentachloronitrobenzene (PCNB) having an initial hexachlorobenzene (HCB) content in excess of 0.1% by weight, which comprises the steps of:
   distilling the impure PCNB at a temperature between about 150° and about 300° C. and at a pressure at or below atmospheric pressure;
   removing an impure distillate product containing PCNB and HCB, wherein the HCB content of said distillate product is in excess of 0.1% by weight; and
   recovering a purified PCNB residue product, wherein the HCB content of said purified PCNB product is less than 0.1% by weight.

2. The process of claim 1, wherein the impure PCNB starting material contains at least one impurity selected from the group consisting of tetrachloronitrobenzenes (TCNB's) and chloronitrobenzenes having fewer than four chlorine atoms per molecule and mixtures thereof in addition to HCB.

3. The process of claim 2, wherein the impure distillate product contains a higher content of TCNBs and a lower content of chloronitrobenzenes having fewer than four chlorine atoms per molecule than does the impure PCNB starting material.

4. The process of claim 1, wherein the distillation temperature is kept between about 150°–250° C.

5. The process of claim 1, wherein the distillation is carried out at a pressure below atmospheric pressure.

6. The process of claim 1, further comprising the step of passing an inert gas through the impure PCNB during the distillation thereof.

7. The process of claim 6, wherein the inert gas is nitrogen.

8. The process of claim 1, wherein the distilling, removing and recovering steps are carried out on a continuous basis.

9. The process of claim 1, wherein the distilling, removing and recovering steps are carried out on a batchwise basis.

10. The process of claim 1, wherein the distilling, of the impure PCNB starting material is continued until from about 5 to about 70% by weight of starting material has been removed as distillate.

11. The process of claim 2, wherein the distillation of the impure PCNB starting material is continued until from about 5 to about 70% by weight of starting material has been removed as distillate.

12. The process of claim 4, wherein the distillation of the impure PCNB starting material is continued until from about 5 to about 70% by weight of starting material has been removed as distillate.

13. The process of claim 5, wherein the distillation of the impure PCNB starting material is continued until from about 5 to about 70% by weight of starting material has been removed as distillate.

14. The process of claim 6, wherein the distillation of the impure PCNB starting material is continued until from about 5 to about 70% by weight of starting material has been removed as distillate.

15. A process for purifying an impure pentachloronitrobenzene (PCNB) composition having an initial hexachlorobenzene (HCB) concentration in excess of 0.1% by weight, which comprises the steps of
   feeding impure PCNB into a distillation zone, said distillation zone being maintained at a temperature on the order of about 100°–300° C. and a pressure up to about 1 atmosphere,
   heating said impure PCNB in said distillation zone to form an impure overhead product having an HCB content in excess of 0.1% by weight and an essentially pure PCNB bottoms products having an HCB content of less than 0.1% by weight; and
   recovering said pure PCNB bottoms.

16. The process of claim 15, wherein said distillation zone is maintained at a temperature on the order of 150°–250° C.

17. The process of claim 16, wherein said distillation zone is maintained under a vacuum.

18. The process of claim 15, where impure PCNB is melted and evaporated in heating zone which is separate from but in fluid communication with the distillation zone, wherein the evaporated impure PCNB is fed from the heating zone to the distillation zone, and wherein an inert gas is bubbled through the impure PCNB in the heating zone to facilitate the feeding of the components of the evaporated impure PCNB from the heating zone to the distillation zone.

* * * * *